United States Patent [19]
Sundström

[11] Patent Number: 5,475,912
[45] Date of Patent: Dec. 19, 1995

[54] METHOD FOR MAKING DENTAL PROSTHESES

[75] Inventor: Erik Sundström, Sandviken, Sweden

[73] Assignee: Sandvik AB, Sandviken, Sweden

[21] Appl. No.: 325,364

[22] PCT Filed: Mar. 26, 1993

[86] PCT No.: PCT/SE93/00253

§ 371 Date: Oct. 26, 1994

§ 102(e) Date: Oct. 26, 1994

[87] PCT Pub. No.: WO93/19686

PCT Pub. Date: Oct. 14, 1993

[30] Foreign Application Priority Data

Apr. 2, 1992 [SE] Sweden .................................. 9201031

[51] Int. Cl.[6] ...................................................... H61C 5/10
[52] U.S. Cl. ........................................... 29/160.6; 433/223
[58] Field of Search .......................... 29/160.6; 433/218, 433/219, 223

[56] References Cited

U.S. PATENT DOCUMENTS 5,062,799 11/1991 Duncan et al. ......................... 433/215
5,106,303 4/1992 Odéet al. .................................. 433/223

FOREIGN PATENT DOCUMENTS 464908 7/1991 Sweden .

Primary Examiner—P. W. Echols
Attorney, Agent, or Firm—Burns, Doane, Swecker & Mathis

[57] ABSTRACT

Method for making dental crowns or onlays, comprising the steps of forming an aluminium foil (14) after the prepared surface (13) of the tooth or the top (23) of a dental post or implant (21), anodic oxidizing the foil all through to oxide foil, firing the oxide foil at temperatures above 700° C. to alpha-corundum and applying a ceramic top layer.

8 Claims, 1 Drawing Sheet

METHOD FOR MAKING DENTAL PROSTHESES

FIELD OF APPLICATION

The invention relates to a method for making ceramic dental crowns, inlays or onlays to replace lost dental natural substance. The tooth is prepared by a dentist, and a copy of the prepared surface is used as a base for building a replacement part of fired ceramic in a dental laboratory. Because of the way the copy is made or utilized, previously known methods cause problems with precision, colour matching and time delays, which are avoided by the present invention.

DISCUSSION OF RELATED ART

Among known methods for making crowns, the most common method is making a copy of the prepared tooth surface by pressing a gold foil against it, removing the foil and firing a ceramic layer on the foil in the laboratory in one or more layers at temperatures low enough not to melt the gold foil. The metal-ceramic part is then secured to the tooth by ionomer or phosphate dental cement. Problems with this method are that the adhesion of the gold foil is weak, requiring that the sides of the prepared surface are steep or parallel, requiring a thin gold foil which is easily damaged and may have inadequate strength for building-up of the ceramic layers. Its edge will be visible as a thin line between the crown and the natural tooth. Platinum foils have higher melting point but otherwise the same problems.

Other known methods create a higher strength base for the crown by making negative and positive models of the prepared surface in several steps, followed by making a metal base by casting or electrolytic deposition, or by copy milling from a block of ceramic material. To facilitate milling, the ceramic block may be fired at a lower temperature than final, or may consist of a pressed but not sintered body of ceramic powder such as aluminium oxide as described in the patent SE 464 908. Disadvantages with these methods are loss of precision because of the number of steps and the shrinkage of the ceramic during final firing or sintering.

It has also been described how to make an impression of the prepared tooth surface with fiberglass weave prepreg, which is subsequently hardened to a base part according to the patent U.S. Pat. No. 5,062,799. With this method there is a great risk of deformation of the weave before hardening, and the ceramic can not be fired directly on the weave.

For all metallic bases, the choice of ceramic is limited by the requirement that the firing temperature must not be so high that the metal softens or deforms.

SUMMARY OF THE INVENTION

According to the invention an impression of the prepared tooth surface is made from soft aluminium metal foil which is subsequently converted to hard and heat-resistant alpha-corundum by electrochemical methods. The corundum foil can then be used as a base for building a ceramic crown or onlay. Since the same foil that was used to make the original impression becomes part of the crown or onlay many copying operations are avoided and the precision is retained. Because of the strength of alpha-corundum a high grade ceramic enamel can be used without firing temperature restrictions. The shape and surface structure of the metal foil can be so closely controlled that the requirement for parallel or very steep prepared tooth surfaces can be relaxed. The metal foil can be relatively thick, up to 0.5 mm, without a visual metal edge on the finished crown.

DETAILED DESCRIPTION OF THE PREFERRED EMBODIMENTS

Figure 1:
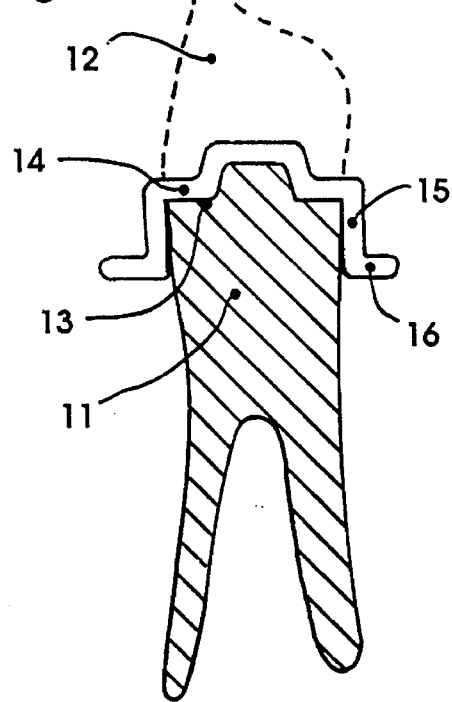
FIG. 1 is a cross section of a tooth being repaired according to present invention.
Figure 2:
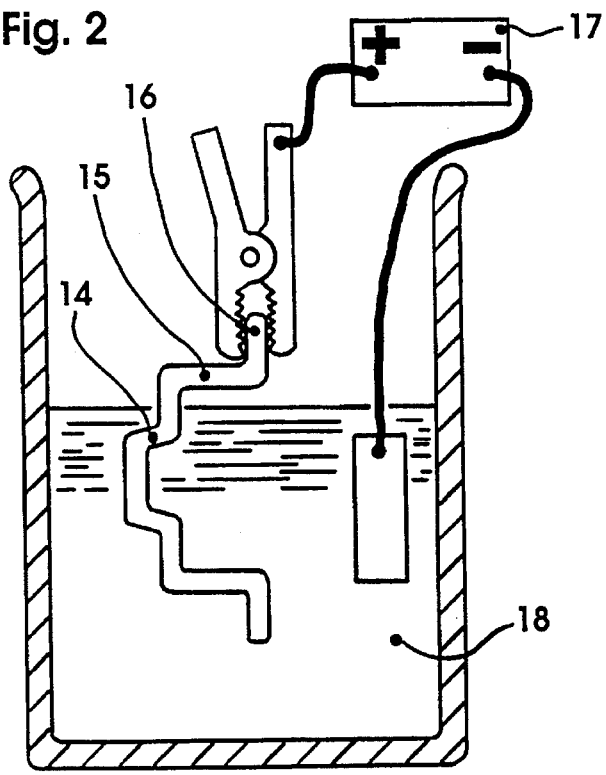
FIG. 2 is a view of a foil in a bath.

FIG. 1 shows a cross-section of a tooth (11) where an upper surface (13) has been prepared after loss and removal of tooth substance (12). An aluminium foil is formed by pressing a first major part (14) of it into contact with the prepared surface (13). A second part (15) of it can advantageously be pressed against the remaining outside of the tooth to increase the stiffness during processing. This second part (15) is to be removed before the crown is finished. The formed aluminium foil is cleaned and etched in an acid such as hydrochloric acid if a coarse surface desired. As shown in FIG. 2 the foil is subsequently converted all through to hydrated aluminium oxide through anodic oxidation in an acid bath (18) containing oxalic acid, sulphuric acid, other acids or mixtures of acids.

Since the thickness distribution of the foil will become unequal during forming, the anodic oxidation should not be performed with the whole foil submerged in the acid bath (18), since that would leave non-converted metal remnants where the thickness was high or where the electric field strength was low. The anodic oxidation should preferrably be performed while the foil is gradually moving through the surface into the acid bath, either by lowering the foil or by raising the acid bath surface. The electric connection should be made to a part (16) of the foil above the acid bath surface, and for this purpose the foil should be made slightly larger than what will be part of the finished crown or onlay.

When the foil is converted to a hydrated aluminium oxide foil it is brittle but can be handled with care. In the plane of the foil the dimensions are the same as the prepared tooth surface (13), since the oxide grows isotactically from the metal surface. In a thickness direction the oxide foil may be thicker or thinner than the aluminium foil depending on the acid bath temperature and content. High temperature and high sulphuric acid content give thinner oxide foil, low temperature and high oxalic acid content give thicker oxide foil. Preferably, the oxide foil should be slightly thinner than the aluminium foil to allow some space for the dental cement layer.

The oxide foil is subsequently fired at a temperature over 700° C., preferably around 900° C., when the oxide is recrystallized to waterless alpha-corundum with unchanged dimensions (34,35). The firing can be made in a conventional muffle oven or with microwave heating, where the latter has the advantage of faster and smoother heating concentrated to those parts where some moisture is left.

Figure 3:
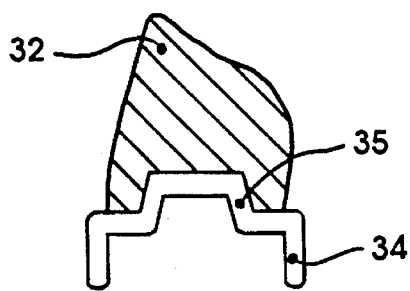
FIG. 3 is a view of a ceramic top mounted on the foil.

On the corundum foil (34,35) the edge parts are ground off or cut by laser, and a ceramic top layer (32) is applied as porcelain enamel or other ceramic. See FIG. 3. The corundum foil is strong and heat resistant up to 1200° C., and high grade wear resistant ceramics with high firing temperatures can be chosen. The corundum surface is naturally coarse, especially if the aluminium foil had been etched. The colour of the corundum foil is white and after grinding of the edge does not contrast with the natural tooth or the ceramic top layer. The thickness of the top ceramic layer (32) can be chosen according to circumstances, thick on crowns with occlusion surface and thin on onlays for restoring the side regions.

Figure 4:
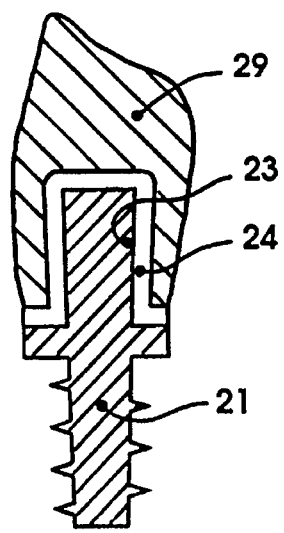
FIG. 4 illustrates a method of attaching a crown to a mounted post.

As shown in FIG. 4 the method can also be used for making crowns to be attached to dental posts or implants (21). In this case the aluminium foil is shaped after the top (23) of the dental post or implant, or a master copy of the top, and can be produced as a standard item. After conversion to alpha-corundum, the foil parts (24) are cut to size and fired with a ceramic top layer (29) adapted to the shape of the adjoining teeth.

If the prepared tooth surface is so sensitive to touch, that it does not permit the limited pressure needed for forming of a soft aluminium foil, the method can be modified by making a negative wax impression of the prepared surface, and from this a positive cement or plaster model, against which the aluminium foil is formed.

For superficial veneer-type restorations on the sides of teeth, it is possible to use the corundum foil without a top layer after thinning of the edge and grinding to the desired surface structure.

The steps in conversion from aluminium foil (14,15) to corundum foil (34,35) can be performed automatically even for single foils in a machine with three compartments and automatic transfer of the foil. The first compartment contains cleaning and etching fluids, and the foil is held in it for a predetermined time. In the second compartment the foil is held in a ceramic frame with connection (16) to an electric source (17) at the upper edge. The foil is slowly lowered into an acid bath (18) while the voltage is controlled, and the lowering speed determined by the electric current. When the whole foil is oxidized except at the electric connection (16) the voltage is suddenly raised and the foil is burnt through at the connection, leaving just the oxide foil in the frame. The third compartment is made as a microwave cavity for firing the oxide foil to alpha-corundum in a predetermined time.

I claim:

1. A method for making dental crowns and onlays, comprising the steps of:

forming an aluminum foil to conform to a prepared surface onto which it will be attached, anodic oxidizing the foil all through to from an oxide foil, firing the oxide foil at a temperature above 700° C. to alpha-corundum, and applying a ceramic top layer to the foil.

2. Method according to claim 1, where the aluminium foil is formed in direct contact with the prepared tooth surface.

3. Method according to claim 1, where the aluminium foil is formed to conform is the top of a dental post or implant.

4. Method according to claim 1, where the oxidizing is performed in an acid bath containing oxalic acid.

5. Method according to claim 4, where the oxidizing is performed while the foil is moving down through the surface of an acid bath.

6. Method according to claim 1, where the oxidizing is performed while the foil is moving down through the surface of an acid bath.

7. Method according to claim 1, where the oxide foil is fired in a microwave cavity.

8. Method according to claim 1, where the foil is cleaned, oxidized and fired in a machine with separate compartments.

* * * * *